United States Patent [19]

Purdy, III

[11] 4,110,433
[45] Aug. 29, 1978

[54] EQUINE RHINOPNEUMONITIS VIRUS

[75] Inventor: Charles W. Purdy, III, St. Joseph, Mo.

[73] Assignee: Philips Roxane, Inc., St. Joseph, Mo.

[21] Appl. No.: 679,840

[22] Filed: Apr. 23, 1976

[51] Int. Cl.$^2$ .................. A61K 39/12; C12K 7/00
[52] U.S. Cl. .................................... 424/89; 195/1.3
[58] Field of Search ........................ 195/1.3; 424/89

[56] References Cited

U.S. PATENT DOCUMENTS 3,725,542  4/1973  Mayr et al. ..................... 195/1.3

Primary Examiner—Sam Rosen

[57] ABSTRACT

A virulent strain of Equine Rhinopneumonitis (ERP) Virus was passed for 50 passages through the Vero Cell Line (monkey Kidney) at 26° C. At the end of this treatment, it had become attenuated so that a vaccine formed from the virus gave none of the usual ERP symptoms when horses were inoculated with the vaccine by the I. M. route, i.e., they showed none of the usual nasal and ocular discharges, no fever, no anorexia and the like. When the vaccinates were challenged with virulent virus, none of the clinical symptoms of Equine Rhinopneumonitis Virus appeared, while unvaccinated control animals, so challenged, contracted ERP within 3-4 days with all the classical symptoms.

The vaccination of a mare prior to breeding and again during her pregnancy will prevent abortions caused by virulent ERP virus. Other horses should be vaccinated once a year in order to prevent the Equine Rhinopneumonitis disease complex. Foals may be vaccinated any time after 1 day of age even in the face of maternal antibody. The ERP Vaccine Virus may be administered parenterally or extra-parenterally to the mucosal surfaces of the body. The I. M. route of inoculation is recommended.

15 Claims, No Drawings

EQUINE RHINOPNEUMONITIS VIRUS

GENERAL DESCRIPTION OF INVENTION

The invention relates to a vaccine for the protection of Equidae against the effects of Equine Rhinopneumonitis, a method of preparation of the vaccine and to a method of protection of Equidae therewith.

Briefly stated, the invention comprises the steps of attenuating a virulent strain of ERP virus by passage through a Vero Cell Line at a reduced temperature for a number of serial passages sufficient to reduce the virulence of the virus without affecting its immunogenic character.

Rhinopneumonitis is an acute viral infection believed to be caused by Type I Equine Herpes Virus, and is characterized by fever, leukopenia, and catharrhal inflammation of the respiratory tract. The viral disease predisposes to secondary bacterial infection which affects various parts of the respiratory tract. Abortion is normally a sequel when pregnant mares are infected.

Rhinopneumonitis occurs on farms in areas of concentrated horse breeding. A relatively uniform pattern is observed in central Kentucky, where both respiratory disease and abortion have been studied. Respiratory disease is observed almost exclusively in young horses, either on farms or when they are assembled for sale or training. Most farms in the area have outbreaks of rhinopneumonitis in the fall or early winter, especially in October, November, and December. The outbreaks in young horses often are associated with weaning and assembling in winter quarters. Mares on the farms have no overt signs of disease at this time, but infection may be demonstrated by serologic tests. The disease spreads rapidly within a stable or training area, with all horses becoming infected within a few days or weeks.

Abortions have been observed in every month except July and August. They are most prevalent in midwinter and early spring. Of 700 abortions recorded in Kentucky, 15% occurred in January, 24% in February, 29% in March, and 18% in April. Abortion may occur from the 5th month of gestation to full term. Some foals infected prenatally are born alive at full term. Data on 623 abortions show 11% occurring in the 8th month, 30% in the 9th month, 36% in the 10th month, and 19% in the 11month. The data indicate a relation between age of the fetus and occurrence of abortion, but the breeding period of mares and the enzootic pattern in young horses have an important influence on the seasonal incidence and age of the fetus at the time of abortion.

The incubation time between nasal inoculation and abortion varies from 3 weeks to 4 months, establishing that the infection which results in abortion is coincident with the earlier enzootic infection of young horses on the farm. The virus spreads readily by direct contact, fomites, and aerosolized secretions. Virus may spread from one mare that aborts to others but in most outbreaks the evidence indicates that nearly all mares on the premises were infected 1 to 4 months before the first abortions occur.

The disease occurs annually in young horses on many farms that have not had new horses introduced, suggesting the presence of carriers among the adult horses. The regularity of outbreaks when young susceptible horses are assembled also indicates a carrier state. Outbreaks are frequent when susceptible horses are assembled for sales, in yards, in training areas, at race meets and in military establishments.

The incubation period of ERP varies from 2 to 10 days. Primary infection of fully susceptible horses is manifested by fever and a serous discharge from the nostrils. Temperatures may reach 106° F, and fever persists for 1 to 7 days in uncomplicated cases. Afternoon temperatures usually are higher than in the morning. Leukopenia occurs in parallel with fever. Both neutrophils and lymphocytes are depressed during the first 2 days of fever. Lymphoocytes return to normal levels in 2 to 4 days, and neutrophils regain normal levels in 5 to 9 days. Feed and water consumption may be reduced. Mild congestion of the nasal mucous membranes is observed, and there may be palpable edema of the mandibular lymph nodes. Enteritis and diarrhea, edema of the legs, and tendovaginitis are infrequent in uncomplicated cases. General depression is slight in horses kept at rest. All signs are exacerbated by forced exercise or work. Recovery is complete in 1 to 2 weeks unless complications develop.

Reinfection may occur at intervals of 4 to 5 months or longer. These subsequent infections are usually asymptomatic, afebrile, and do not result in complications, especially in adult horses on breeding farms. The effect of reinfection on horses in racing or subjected to hard work is not known.

The vaccine of the present invention is an attenuated form of the virus prepared from a virulent strain of Equine Rhinopneumonitis (ERP) Virus which was passed for 50 passages through the Vero Cell line (monkey kidney) at 26° C.

SUMMARY OF INVENTION

Briefly stated, the invention relates to a vaccine which is prepared by a process which comprises the steps of innoculating a tissue cell culture with a virulent strain of ERP virus so that reproduction of the virus will occur, serially passing the virus so propagated in additional tissue cell cultures for a sufficient number of passes and under conditions such that the virus becomes attenuated to an avirulent condition without losing its immunogenic character.

Attenuation, or modification of the virulent or pathogenic character of bacteria or a virus to an avirulent or nonpathogenic state is well known in the art.

Modification or attenuation of morphology and/or pathogenicity has been brought about by many techniques. Sometimes repeated serial passage in the host tissue attenuates the organism; serial passage in a tissue which is different from the host tissue sometimes leads to attenuation; chemical shock to the organism, radiation treatment, low temperature passage, and other techniques have been used by the bacteriologist and the virologist to produce pathogenically inert organisms which retain their ability to cause their hosts to form antibodies or cell mediated immunity capable of effectively neutralizing a pathogen. The attenuation without loss of immunogenicity of a living organism is completely non-predictable and only empirical methods may be used to determine efficacy of any given technique. For example, a given technique that has been found applicable to one type of virus may not always be projected as being applicable to another. Prior art techniques for attenuation of a virulent strain of ERP virus has been reported. For example, serial passage of a virulent ERP is hamster tissue with some adaptation has been reported by E. R. Doll in Vet. Bull. 32, 1943. U.S.

Pat. No. 3,725,542 described the attenuation of a virulent strain of ERP virus by cultivating and multiplying rhinopneumonitis viruses, deprived from a source selected from infected horses, infected foals, and aborted horse fetuses, in susceptible tissue selected from susceptible organs, (such as monkey kidney) susceptible test animals, and susceptible permanent cell lines suitable for the cultivation and multiplication of said viruses, said multiplying involving from three to 10 passages; completely attenuating the viruses until they have lost pathogenicity for the horse by serial passage through the primary cell cultures obtained from sheep, pigs and piglets and from stable permanent cell lines derived from these primary cell cultures.

It is postulated that immunogenic protection against subsequent challenge by a virulent ERP virus does not occur unless the avirulent virus reproduces itself in the host animal and can be recovered and identified after vaccination occurs. To date, none of the attenuated virus strains reported possess this characteristic and do not furnish the desired degree of protection.

It has now been found, however, and forms the object of this invention, that if the stable cell line from the African Green Monkey, *Cercopithecus aethiops*, the Vero call line, is inoculated with a virulent ERP virus and serially passed in such a cell line at reduced temperatures, say 23° to 33° C, the virus becomes attenuated and non-virulent but still retains its immunogenic character, that is, when introduced into an equine host, will trigger its immunological mechanism to produce viral antibodies and cell mediated immunity. The animal then becomes immune to subsequent infection, and the avirulent virus can be recovered from the vaccinated animal and identified.

Using ordinary serial passage techniques which are standard in the art, it has been found that the desired avirulent character has been developed without loss of immunogenicity after about 30-60 passes at a temperature within the range of from about 23° to about 33° C. However, up to about 250 or 300 passage or more may be used.

The ERP vaccine of this invention may be administered to any species of the family Equidae by either extra - or interparenteral techniques. The vaccine, in liquid form, may be given intra-nasally, intra-orally, intra-ocularally, intra-muscularly, intra-venously, intra-peritoneally and the like. In a dry powdered form it is suitable for extra-parenteral administration. As is usual with vaccines of this type, from about 3,000 to 100,000 $TCID_{50}$ units are administered in a single dose.

DETAILED DESCRIPTION OF INVENTION

The steps of the inventive process may be more clearly described as follows:

1. Reproduction of Virus

Tissue cell cultures were prepared using Vero stable cell line derived from African Green Monkey at a passage level of 129. A standard glass culture vessel was seeded with a trypsinized suspension of Vero cells containing sufficient media to cover the cells to a depth of about ½ inch. Eagles Minimum Essential Medium (MEM), as defined in Handbook of Cell and Organ Culture by Merchant, et al., Burgess Publishing Co., 1964, containing 10% fetal calf serum for growth medium (5% in maintenance medium) was used.

However, any standard growth medium may be used, such as Lactalbumen Hydrolysate Medium in Hanks Balanced Salt Solution, Medium 199, etc. The culture vessels were incubated at 37° C. for from 1-3 days after which time a monolayer of Vero cells was formed.

The vessel was then inoculated with equine Herpes I, identified as an A183 isolate obtained from the University of California, using standard aseptic techniques and after 24-72 hours incubation at 37° C., the cytopathology of the cells was substantially complete indicating that the virus had reproduced itself. The virus was passaged 13 times in Vero cells at 37° C. as above and then subjected to the attenuation procedure as detailed below.

ATTENUATION

Using standard tissue culture flasks and the MEM growth medium described above, monolayers of Vero cells were prepared. About 100 $TCID_{50}$/ml of the 13th passage virus was introduced into the flasks and the inoculated flasks were incubated at a temperature of 26° C. After about 8-10 days a small area of cell degeneration was noted and a second serial passage was made with some of the fluid medium. Incubation at 26° C. continued and cellular cytopathology increased. After each serial passage, cytopathology increased and after about 30-60 serial passages, cytopathology was found to be complete after 3-5 days incubation at 26° C. This attenuated virus was identified as A183 V26 P50 ERP vaccine.

The following in vivo experiments were carried out with the 50th or the 55th passage of the cold adapted virus. All ERP vaccine virus was administered deep I.M.

A virulent ERP challenge was produced by serially passing the unattenuated A183 virus in nasal washes and whole blood through four horses. The equine passaged virus induced classical rhinopneumonitis symptoms of ERP as well as abortions in pregnant animals. The challenge ERP virus pool was used repeatedly for challenge of experimental horses with excellent results in non-immune animals. All challenge virus was administered intranasally.

Serum neutralization tests were used to measure all serological responses to the ERP vaccine or challenge virus.

The purity of ERP vaccine virus produced as described above is determined by neutralizing the cyto-pathogenic effect (CPE) produced in tissue culture with known equine Herpes I typing serum.

The vaccine virus produces large syncytium in $RK_{13}$ cells and Vero cells at 37°. The syncytium can be used as a marker for the vaccine virus at the virulent ERP challenge virus produces individual cell rounding type CPE, in the above cell lines at 37° C.

The vaccine virus kills newborn hamsters and the vaccine virus was recovered from the dead hamsters producing the same type of syncytial marker. No clinical symptoms of equine viral diseases were induced in vaccinated horses or foals in varying age groups.

The vaccine virus can be isolated from equine peripheral leukocytes from 2 to 11 days following ERP vaccination. Other virus agents are not isolated following vaccination, except the virus recovered from the horses has the vaccine marker (syncytium).

The experimental vaccine virus A183 V26 P50 was checked for the following adventitious viral agents by known techniques, and none was found to be present: Equine infectious Anemia virus, Equine Herpes II group of viruses, Equine Adeno virus, Equine Encephalomyelitis virus group and Equine Influenza group (A/Equi/1; A/Equi/2).

PREPARATION OF VACCINE

The attenuated virus prepared as described above, was grown in large quantities using the same growth medium described above in standard monolayer Vero cells flasks. The flasks were incubated until cytopathology was completed, usually in from 3-4 days. The growth medium was then harvested and admixed with a stabilizing solution and divided into unit doses of approximately 1,000 to 10,000 $TCID_{50}$/ml each in the usual vaccine vials. The material was then freeze-dried in the vials and sealed for use.

EXPERIMENT I

The following experiment was designed to determine if the ERP vaccine developed was safe and to see if the vaccine virus transmitted to contact horses. In addition, the efficaciousness of the vaccine in vivo was to be tested against the challenge virus.

A group of 6 mixed breed horses of both sexes were housed under the same roof in a group pen. Feed consisted of oats and grassy hay and self-feeding waterers were present. The group received the attenuated ERP vaccine. All vaccinations were given deep I.M. The first vaccination was followed by a similar vaccination in 28 days. All horses were challenged with virulent ERP virus 56 days following the first vaccination. The following parameters were monitored; all horses were checked daily for clinical signs of ERP and temperatures and serums were monitored throughout the test. Three horses were selected to monitor virus isolations from the buffy coat cells and nasal swabs. Virus isolations were started on two contact controls at the time of challenge. Complete blood counts were frequently made on the horses being monitored for virus isolations.

Bacterial isolations and identification were frequently made on horses exhibiting nasal drainage. Principals were number 104, 77, 52, 53 and 54. Contact control was number 79. Results are shown in Experiment I tables below:

EXPERIMENT I
Serum Neutralizations
Vaccinated Twice I.M.

| | 1st Vac. | +12 days | +21 days | 2nd vac. +28 days | +12 days 2nd vac. | +20 days 2nd vac. | Challenge +28 days 2nd vac. | +11 days Challenge | +21 days Challenge | +29 days Challenge | +66 days Challenge |
|---|---|---|---|---|---|---|---|---|---|---|---|
| P52 | 16 | 128 | 512 | 256 | 128 | 512 | 256 | 512 | 512 | 1024 | |
| P53 | 8 | 256 | 512 | 1024 | 128 | 512 | 128 | 256 | 128 | 256 | |
| P54 | 4 | 64 | 512 | 256 | 256 | 256 | 128 | 512 | 128 | 256 | |
| P77 | 0 | N.D. | 2048 | 512 | 256 | 256 | 128 | 1024 | 256 | 256 | |
| P104 | 0 | 0 | 64 | 8 | 64 | 128 | 128 | 256 | 256 | 128 | |
| C79 | | 0 | 0 | 0 | 0 | 0 | 0 | 512 | 2048 | 2048 | |

P = Principal
C = Contact Control
None of the principals in this experiment had any clinical signs of ERP

EXPERIMENT I
Equine Herpes Virus Isolation

| | 1st Vaccination | | | | | | | | | | 2nd Vaccination | | | | | | | | Challenge | | | | |
|---|---|---|---|---|---|---|---|---|---|---|---|---|---|---|---|---|---|---|---|---|---|---|---|
| | 0 day | +3 | +4 | +5 | +6 | +7 | +10 | +12 | +14 | +28 | +3 | +5 | +6 | +7 | +8 | +12 | +14 | +28 | +1 | +2 | +3 | +4 | +7 |
| P77 BC | | | I | I | | I | | | | | | | | | | | | | | | | | |
| NS | | | | | I | | +I | II | | II | | | | | | | | | | | | | |
| P104 BC | | II | II | I | II | | II | II | | NOT DONE | | | | | | | | | | | | | |
| NS | +8 | | | | | | | | | | | | | | | | | | | | | | |
| C79* BC | +9 | +10 | +11 | +14 | +16 | +18 | +21 | | | | | | | | | | | | | | | | |
| NS | I | | II | II | II | II | II | | | | | | | | | | | | | | | | |

| | P77 BC | | | | | | | | | | | | | | |
|---|---|---|---|---|---|---|---|---|---|---|---|---|---|---|---|
| NS | | | | | | | II | | | | | | | | |
| P104 BC | | | | II | | | | | | | | | | | |
| NS | II | II | II | II | II | | | | | | | | | | |
| C79* BC | I | | | | | | | | I–II | II | II | II | I | II | +I–I |
| NS | II | | | | | | | | | | | | | I | +I |

*Abortion 15 days following challenge
Herpes I Virus recovered from fetus.
I = Equine Herpes I Virus
II = Equine Herpes II Virus
+ = Unidentified Virus
P = Principal
C = Contract Control
BC = Buffy Coat
NS = Nasal Swab An examination of the data reported in the TABLES of Experiment I above plus the absence of clinical signs indicate the following:
1. The vaccine did not induce disease symptoms following either vaccination.
2. The vaccine virus did not transmit to the contact control animals over a 56 day period of being held together, prior to challenge. There were numerous isolations of equine Herpes II virus throughout this experiment.

Although the control, C 79, demonstrated the normal clinical symptoms of Equine Rhinopneumonitis, that is inflammation of the respiratory tract, anorexia and general malaise, a temperature increase to several degrees above normal within two days after challenge with virulent virus, and a severe depression of the white blood cell count, the vaccinated principals were protected against the virulent challenge virus as measured by lack of clinical symptoms, normal body temperatures and normal white blood cell counts.

EXPERIMENT 2

The following experiment was designed to determine if the attenuated ERP vaccine was safe in pregnant mares (no clinical symptoms or abortions) and to determine the efficacy of the vaccine in pregnant animals against a virulent ERP challenge, to obtain information concerning ERP passive antibody transferred to the foals, the safety of the vaccine at different time intervals of pregnancy, and to determine if the vaccine virus would transmit to contact controls which were non-vaccinated pregnant animals.

Experiment 2 was divided into four groups of pregnant horses. Two groups were vaccinated once and challenged intranasally 40 days later with virulent ERP virus. One of the aforementioned groups received the 50th passage level of the cold adapted vaccine virus. The remaining two groups of pregnant horses were vaccinated twice, 20 days apart in a similar manner as above with the same passaged levels of cold adapted vaccine virus. The latter two groups were challenged intranasally 50 days following the first vaccination. A fifth group was used as challenge control horses and foals.

The following parameters were measured: temperature, virus isolations and identification, CBC, serum neutralization titers and clinical symptoms. The above parameters were measured in both the mares and foals. The foals were monitored for virus from blood leukocytes and nasal turbinates immediately upon being found and two or three days after birth. Also, serums were collected at the time of foaling of the newborn colts and weekly thereafter. In some cases, burlap barriers were placed over the mammary gland to prevent suckling after parturition, in order to assure some precolostrum serum samples. ERP colostrum neutralizing antibody was measured in some areas. Also, many paired serum samples were collected from colts and mares at birth or later.

Many of the foals born during this experiment were vaccinated with the attenuated ERP vaccine virus at 10 to 21 days of age, and this data will be reported from a safety point of view in Experiment 3. Data obtained from this Experiment are set out in the Experiment 2 TABLES below.

EXPERIMENT 2
ERP Serum Neutralizations and Pertinent Data

| I.D. No. | 2/8/74 1st vac 0 day | +7 | +14 | 3/1/74 2nd vac +21 | +5 | +14 | 4/2/74 Chall. +32 | +6 | +14 | +21 | Live Del. | Abort. | Death After Del. | #Days Post Vac. Birth Occurred | #Days Post Chall Birth Occurred | Virus Recovery from foal or Fetus | Foal Neutralizing Ad Titers 3-14 Days of Age |
|---|---|---|---|---|---|---|---|---|---|---|---|---|---|---|---|---|---|
| Group 1 - Pregnant Mares Vaccinated Twice with A183-V26-P50 Virus |||||||||||||||||
| P65 | 16 | | 512 | 1024 | 512 | 512 | | born 1 day | pre | chall. | 3/27/4 | - removed | | 47 | NA | — | 256 |
| P75 | 16 | | 512 | 512 | 256 | 256 | | 256 | 256 | 256 | 5/4/4 | | | 85 | 32 | — | 1024 |
| P150 | 0 | | 128 | 128 | 256 | 128 | | born 3 day | pre | chall. | 3/30/4 | - removed | | 50 | NA | — | 128 |
| P155 | 4 | | 256 | 512 | 512 | 256 | | 256 | 256 | 512 | 5/20/4 | | | 101 | 48 | — | 512 |
| P157 | 8 | | 256 | 256 | 512 | 512 | | 256 | 256 | 64 | 4/21/4 | | | 72 | 19 | — | 512 |
| C140* | >32 | | 16 | >16 | 16 | 16 | | 32 | 32 | 1024 | Male | | | NA | NA | NA | NA |
| C74 | | | | Preg. Horse added at Chall | | | | >16 | 4 | 1024 | 4/7/4 | | | 58 | 5 | — | 4 |
| Group 2 - Pregnant Mares Vaccinated Twice with A183-V26-P55 Virus |||||||||||||||||
| P151 | 4 | | 512 | 1024 | 128 | 128 | | 256 | 128 | 256 | 5/13/4 | | | 94 | 41 | — | 128 |
| P152 | 8 | | 64 | 128 | 128 | 128 | | 256 | 128 | 128 | 4/22/4 | | | 73 | 20 | — | 16 |
| P153 | 2 | | 128 | 128 | 128 | 128 | | 128 | 512 | chall. | 3/27/4 | | | 47 | NA | — | 128 |
| P154** | 2 | | 128 | 256 | 256 | 128 | | Colt born 6 day | pre | 512 | 4/28/4 | - removed | 4/30/4 | 79 | 26 | NA | NA |
| P156 | 4 | | 512 | 512 | 512 | 2048 | | 512 | 512 | 512 | Not Preg | | | NA | NA | NA | NA |
| C148* | 8 | | 8 | 8 | 8 | 8 | | >2 | >1024 | 1024 | Male | | | NA | NA | NA | NA |
| C159 | | | | Preg. Horse added at Chall | | | | | 16 | 4 | NA | 4/19/4 | | NA | 17 | I | NA |

Group 3 - Pregnant Mares Vaccinated Once with A183-V26-P50 Virus
Chall. 4/1/74

| I.D. No. | 2/20/74 0 day | +7 | +14 | +21 | +40 | +14 | +7 | +14 | +21 | +35 | Live Del. | Abort. | Death After Del. | #Days Post Vac. Birth Occurred | #Days Post Chall Birth Occurred | Virus Recovery from foal or Fetus | Foal Neutralizing Ad Titers 3-14 Days of Age |
|---|---|---|---|---|---|---|---|---|---|---|---|---|---|---|---|---|---|
| P160 | 2 | 64 | 128 | 256 | 256 | 256 | 256 | 256 | 128 | 128 | 4/5/4 | | | 44 | 4 | — | 128 |
| P161 | 16 | >64 | 16 | 1024 | 1024 | 1024 | 512 | 256 | 256 | 256 | 2/23/4 | | 2/23/4(1) | 3 | NA | — | NA |
| P162 | 2 | >64 | 64 | 512 | 1024 | 512 | 256 | 512 | 128 | 128 | 4/5/4 | | | 61 | 21 | — | 64 |
| P164 | 16 | 128 | 64 | 512 | 512 | 128 | 512 | 512 | 1024 | 1024 | 6/24/4 | | | 123 | 83 | — | NA |
| P165 | 4 | 16 | 64 | 512 | 256 | 512 | 1024 | 512 | 512 | 256 | 5/15/4 | | | 44 | 44 | — | 64 |
| C163 | 8 | 32 | 16 | 32 | 256 | 256 | 256 | 256 | 256 | 256 | 4/16/4 | | | 55 | 15 | — | 512 |
| C158 | | | | Preg. Horse added at Chall | | >32 | >2 | 4 | 1024 | 1024 | 4/9/4 | | | NA | 8 | — | NA |

Group 4 - Pregnant Mares Vaccinated Once with A126-V126-P55 Virus

| I.D. No. | 0 day | +7 | +14 | +21 | Chall | +7 | +14 | +21 | +35 | Live Del. | Abort. | Death After Del. | #Days Post Vac. Birth | #Days Post Chall Birth | Virus Recovery | Foal Titers |
|---|---|---|---|---|---|---|---|---|---|---|---|---|---|---|---|---|
| P166 | 0 | 4 | 256 | 256 | 128 | 128 | 64 | 16 | 32 | NA | 2/19/4(2) | | NA | NA | — | NA |
| P167 | 2 | >64 | 1024 | 1024 | 8 | 512 | 512 | 512 | 512 | Preg | | | | | | |
| P169 | 4 | >64 | 128 | 512 | 2 | 256 | 128 | 128 | 64 | 4/5/4 | | | 44 | 4 | — | 8 |
| P170 | 32 | 128 | 256 | 1024 | 32 | 512 | 256 | 256 | 128 | 6/23/4 | | | 122 | 82 | — | — |
| P171 | 4 | 64 | 128 | 64 | 0 | 64 | 64 | 64 | 512 | 5/27/4 | | | 96 | 56 | — | 1024 |
| C168 | 16 | 8 | 4 | <4 | 16 | 32 | 1024 | >1024 | 512 | Preg? | | | | | | |

Group 5 - ERP Serum Neutralization Titers on Challenge Control Horses and Foals

| | Chall | +7 | +14 | +21 |
|---|---|---|---|---|
| C119 | 128 | 64 | >512 | 128 |
| CM174 | 8 | 16 | 4 | 2 |
| CC174 | 2 | 0 | >16 | 256 |
| CM175 | 32 | 32 | >16 | 32 |
| CC175 | 0 | 0 | 512 | |

*C140 and C148 animals were male contact controls
**Mare 154 did not care for her foal
(1)Died during delivery
(2)Aborted 1 day before vaccination
P = Principal
C = Control
CC = Challenge Colt
CM = Challenge Mare The tables in Experiment 2 above shows the safety and the efficacy of the attenuated ERP vaccine of the present invention. The horses were vaccinated and challenged and the date of Groups 1 and 2 which were vaccinated twice and Groups 3 and 4 which were vaccinated once, show both the safety and the efficacy of the attenuated ERP vaccine in the pregnant mares during and after pregnancy and no positive equine Herpes I vaccine virus was isolated from the newborn foals.

VIRUS ISOLATION TABLES

The number of ERP virus isolations following first and second ERP vaccinations are compared in the Virus Isolation Data Tables below. The number of ERP virus isolations made following vaccination and challenge are compared between vaccinates and control animals.

TABLE IV

Equine Herpes Virus Isolations

Group 1 (A183-V26-P50) - Vaccinated Twice I.M.

| I.D. | | 1st Vac 0 Day | +3 | +5 | +7 | +10 | +12 | +14 | 2nd Vac 0 Day | +3 | +5 | +7 | +10 | Chall +14 0 Day | +2 | +6 | +7 | +9 | +11 | +14 | +17 | +21 | +23 | +28 | +48 |
|---|---|---|---|---|---|---|---|---|---|---|---|---|---|---|---|---|---|---|---|---|---|---|---|---|---|
| P65 | BC | | I | I | | | | | | | | | | | | | | | | | | | | | |
| P70 | BC | | | | | | | | | | | | | | | | | | | | | | | | I |
| P150 | NS | | | | I | I | I | | | | | | | | | | | | | | | | | | |
| | BC | | | | | | | | | | | | | | | | | | | | | | | | |
| P155 | NS | | | | I | I | I | I | | I | | | | | | | | | | | | | | | |
| | BC | | | | I | I | I | I | | I | | | | | | | | | | | | | | | |
| P157 | NS | | | | | I | I | | | | | | | | | | | | | | | | | | |
| | BC | | | | | | | | | | | | | | | | | | | | | | | | |
| C140 | NS | | | | | | | | | + | + | | | | | I | I | I | | | | | | | |
| | BC | | | | | | | | | | + | + | | | | I | I | | | | | | | | |
| C74 | NS | | | | | | | | | | | | | | | | | | | II | | | | | |
| | BC | | | | | | | | | | | | | | | | | | | | | | | | |

Group 2 (A183-V26-P55) - Vaccinated Twice I.M.

| | | 0 Day | +3 | +5 | +7 | +10 | +12 | +14 | 0 Day | +3 | +5 | +7 | Chall +14 0 day | +2 | +4 | +6 | +7 | +9 | +11 | +14 | +17 | +21 | +28 | +48 |
|---|---|---|---|---|---|---|---|---|---|---|---|---|---|---|---|---|---|---|---|---|---|---|---|---|
| P151 | BC | | | | | | | I | | | | | | | | | | | | | | | | | |
| | NS | | | | | | | I | | | | | | | | | | | | | | | | | |
| P152 | BC | | I | | I | I | | | | | | | | | | | | | | | | | | | |
| | NS | | | | I | I | | | | | | | | | | | | | | | | | | | |
| P153 | BC | II | | | I | II | | | | II | | | | | | | | | | | | | | | |
| | NS | | | | I | | | | | | | | | | | | | | | | | | | | |
| P154 | BC | | | | I | | | | | | | | | | | | | | | | | | | | |
| | NS | | | | I | | | | | | | | | | | | | | | | | | | | |
| P156 | BC | | | | | | | | | | | | | | | | I | | | | | | | | |
| | NS | | | | | | | | | | | | | | | | | I | | | | | | | |
| P148 | BC | | | | + | | | | | | | | | II | II | | I | | I | I | | | | | II |
| | NS | II | | II | + | | | | | | | | | | | | I | | I | I | | | | | |
| P159 | BC | | | | | + | | | | | | | | | | | I | I | I | I | I | I | | | |
| | NS | | | | | | | | | | | | | | | | | | I | I | I | I | | | |

Group 3 (A183-V26-P50) - Vaccinated One I.M.

| I.D. | | Vac. | +5 | +7 | Chall. +14 0 day | +2 | +4 | +6 | +7 | +9 | +11 | +14 | +17 | +21 | +28 | +48 |
|---|---|---|---|---|---|---|---|---|---|---|---|---|---|---|---|---|
| P160 | BC | | I | | | | | | | | | | | | | |
| | NS | | I | I | | | | | | | | | | | | |
| P161 | BC | | I | I | | | | | | | | | | | | |
| | NS | | | I | | | | | | | | | | | | |
| P162 | BC | | I | | | | | | | | | | | | | |
| | NS | | | | + | | | | | | | | | | | |
| P164 | BC | | | | | | | | | I | I | | | | | |
| | NS | | | | | | | | | I | I | I | | | | |
| P165 | BC | | | | | | | I | I | I | I | I | | | | |
| | NS | | | | | | | I | I | I | I | I | | | | |
| C163 | BC | | | | | | I | I | | | | | | | | |
| | NS | | | | | | I | | | | | | | | | |
| C158 | BC | | | | | | | | | | | | | | | |
| | NS | | | | | | | | | | | | | | | |

Group 4 (A183-V26-P55) Vaccinated Once I.M.

| P166 | BC | | I | | | | | | | | | | | | | |
| | NS | | | | | | | | | | | | | | | |
| P167 | BC | | I | I | | | | | | | | | | | | |
| | NS | | I | I | | | | | | | | | | | | |

TABLE IV-continued

| I.D.# | | | | | | | | | |
|---|---|---|---|---|---|---|---|---|---|
| P169 | NS | | | | | | | | |
| | BC | | | | | | | | |
| P170 | NS | | | | | | | | |
| | BC | | | + | | | | | |
| P171 | NS | | | | | | | | |
| | BC | | | | | I | I | | |
| C168 | NS | | | | | | | I | I |

GROUP 5 - ERP Challenge Control Horses and Foals

| I.D.# | | Chall. 0 Day | +3 | +4 | +5 | +7 | +9 | +12 | +14 | +21 | +28 |
|---|---|---|---|---|---|---|---|---|---|---|---|
| C119 | BC | II | | | | | | | | | |
| | NS | | | | I | I | I | | | I | |
| CM174 | BC | | I | | | | I | | I | | |
| | NS | | I | | | | | | | | |
| CC174 | BC | | | | | + | + | I | | | |
| | NS | | | | I | I | I | I | | | +28 |
| CM175 | BC | | I | | | | | | | I | |
| | NS | | | | | | | | | | |
| CC175 | BC | | | | | I | I | | I | | |
| | NS | | | | | | I | I | | | |

*Herpes I Isolation Made at Parturition
CM = Challenged Mare
CC = Challenged Colt
BC = Buffy Coat
NS = Nasal Swab
P = Principal
C = Control
I = Equine Herpes I Virus
II = Equine Herpes II Virus
+ = Unidentified Virus Examination of the data reported in Groups 1 to 5 of Table IV above indicate the following:

1. The ERP vaccine was safe when used in pregnant animals in varying stages of pregnancy.

2. The pregnant mare vaccinates were protected from abortion and ERP symptoms following challenge. Three principal progeny died. One abortion occurred one day prior to vaccination and the start of the experiment. One foal died two days following birth from a neglectful mother and one foal died during delivery from a first foal mother. Equine Herpes I virus was not recovered from these three progenies. The two deaths which occurred while on test were attributed to chance and in no way connected with ERP, no equine Herpes I isolates were recovered from the blood leukocytes or nasal turbinates from these foals.

3. The 12 challenge controls exhibited typical ERP symptoms — depression, febrile response, anorexia and leukopenia. Five suspected pregnant control mares presented one abortion and a dead foal at one day of age. Challenge virus was recovered from both of these progenies. Two mares presented live normal foals; one fifteen days and the other, five days following challenge. No challenge virus was recovered from these two foals. It is questionable whether the remaining challenge mare was pregnant.

4. Substantial ERP passive immunity was passed in the colostrum to the progenies providing there was adequate time between challenge and parturition.

5. Based on non-rising ERP neutralizing serologies and negative virus isolation, the vaccine did not transfer to the two contact control mares or to the two stallions kept in confinement.

Experiment 3

The following experiment was designed to give information concerning (a) safety of the vaccine in foals, as exhibited by signs and clinical pathology examinations; (b) determine when a foal may be vaccinated in the face of maternal antibody; (c) what type of virus isolation pattern results in a two week old vaccinated foal; (d) efficaciousness of the ERP passive antibody.

The following parameters were measured in Experiment 3, Groups 1 through 4: body temperature, CBC, virus isolations from the nasal turbinates and blood leukocytes, ERP neutralizing serologies and daily observations for clinical signs of disease.

Group 1 - Colt ERP Vaccination Response

This group of eight colts came from mares with a well documented history concerning their ERP status. The foals were I.M. vaccinated with a single freeze dried 1 ml dose of A183 V26 P55 ERP vaccine containing $10^{5.8}$ logs of virus/0.2 ml which was reconstituted with 2 ml of sterile water prior to use.

Group 2 - Colt ERP Vaccination Response (a) Colt number 6 was an orphan colt. No ERP history was available on the orphan's mother.

(b) Colt number 74 came from a challenge control mare which delivered a foal five days after an intranasal challenge of virulent ERP virus. The challenge virus was isolated from the mare, however, no ERP virus was isolated from the foal after parturition. It was apparent that no increase in ERP colostrum antibody occurred in the short interval prior to birth, after challenge.

Group 3 - Colts Challenged IN with Virulent ERP Virus

This group of colts consisted of four colts which were challenged intranasally by catheter with 10 ml of virulent ERP virus which contained $10^{2.7}$ logs of virus/0.2 ml. The ERP history of the mares involved was well documented.

Group 4:

This group consisted of two colts coming from mothers with unknown ERP histories. The colts were challenged in a similar manner as the colts in Group 3.

The results of this experiment are set out in the TABLES below.

EXPERIMENT 3

Colt and Mare Data Sheet
Group 1: Colt Vaccinates (from Mares Vaccinated &/or Challenge Prior to Foaling) Receiving One I.M. Dose of A-183 V26 P55 Virus

| Mare & Colt No. | Group Designation | Status of Mare at Parturition | | | Colt's ERP Neutralizing Antibody Titer | | |
|---|---|---|---|---|---|---|---|
| | | Days Post First Vacc. | Days Post Challenge | ERP Neut. Titer | Hours or Days Post Parturition | | Age and Neutralizing Ab Titer at time of Vaccination and/or Challenge |
| | | | | | 0 to 16 hrs. | 3 to 10 days | |
| 48 | 1 × Vac., no Chal. | 59 | NA | 512 | 0 | 256 | 11 days- |
| 65 | 2 × Vac., no Chal. | 47 | NA | 512 | 1024 | 256 | 23 days-512 |
| 151 | 2 × Vac., Chal. | 94 | 41 | 256 | 0 | 128 | 9 days-128 |
| 152 | 2 × Vac., Chal. | 73 | 20 | 128 | 4 | 16 | 10 days-16 |
| 162 | 1 × Vac., Chal. | 61 | 21 | 256 | 32 | 64 | 10 days-64 |
| 163 | 1 × Vac., Chal. | 55 | 15 | 512 | 4 | 512 | 22 days-64 |
| 165 | 1 × Vac., Chal. | 84 | 44 | 128 | 32 | 64 | 7 days-64 |
| 171 | 1 × Vac., Chal. | 96 | 56 | 256 | 512 | 1024 | 9 days-1024 |
| Group 2: Vaccinated Colts | | | | | | | |
| Sub Group A (no history on mare) | | | | | | | |
| 6 | No Vac., no Chal. | NA | NA | Info not available | Info not available | 128 | 22 days-64 |
| Sub Group B (time inadequate for transfer of passive Ab from mare to foal) | | | | | | | |
| 74 | No. Vac., Chal. | NA | 5 | 16 | 0 | 4 | 31 days-4 |
| 68 | Chal., 1 × Vac. | 78 | 483 | 512 | 512 | 1024 | 13 days-256 |
| 70 | 2 × Vac., Chal. | 85 | 32 | 0 | 1024 | 1024 | 11 days-512 |
| 155 | 2 × Vac., Chal. | 101 | 48 | 512 | 0 | 32 | 16 days-64 |
| 157 | 2 × Vac., Chal. | 72 | 19 | 128 | 32 | 512 | 11 days-512 |
| Group 4: Challenge Control Colts (from Non-Vaccinated & Non-Challenged Mares) Receiving Wild Type A183 Virus I.N. | | | | | | | |
| 174 | NA | NA | NA | Info not available | Info not available | Info not available | 14 days-0 |
| 175 | NA | NA | NA | " | " | " | 20 days-0 |

EXPERIMENT 3 - PART B

FOAL VIRUS ISOLATION IDENTIFICATION AND/OR CHALLENGE

GROUP 1 - Vaccinates:

| | +3 | +5 | +7 | +9 | + | +12 | +13 | +14 | +21 | +27 |
|---|---|---|---|---|---|---|---|---|---|---|
| BC 48 NS | | | I | + | | | | | | |
| BC 65 NS | | | I | | | | | | | |
| BC 151 NS | | | I | + | | | | | | |
| BC 152 NS | I | I | I | | I | | | | | |
| BC 162 NS | | I | I | | | | | | | |
| BC 163 NS | | | | I | I | I | | | | |
| BC 165 NS | | I | I | I | | | | | | |
| BC 171 NS | | | I | I | | | | | | |

GROUP 2 - Vaccinates:

| | +3 | +5 | +7 | +9 | + | +12 | +13 | +14 | +21 | +27 |
|---|---|---|---|---|---|---|---|---|---|---|
| BC 6 NS | | + | + | | | | | | | |
| BC 74 NS | I | I | I | II | II | II | | II | | |

GROUP 3 - Foals with Passive ERP Ab - Challenged:

| | +3 | +5 | +7 | +9 | + | +12 | +13 | +14 | +21 | +27 |
|---|---|---|---|---|---|---|---|---|---|---|
| BC 68 NS | | | I | | | I | | | I | |
| BC 70 NS | | I | I | | | | | | I | |
| BC 155 NS | | I | I | I | | I | | | I | |
| BC 157 NS | | I | | | | | | I | | |

GROUP 4 - Challenge Control Foals

| | +3 | +5 | +7 | +9 | + | +12 | +13 | +14 | +21 | +27 |
|---|---|---|---|---|---|---|---|---|---|---|
| BC 174 NS | I | I | + | + | | I | | I | | |
| BC 175 NS | I | I | I | I | | I | I | I | | |

I = Equine Herpes I Virus
II = Equine Herpes II Virus
+ = Unidentified Virus

None of the vaccinated foals showed any adverse clinical signs. Occasionally, Streptococcus zooepidemicus bacteria was isolated from nasal passages during infrequent nasal drainages which had no pattern in relationship to the ERP Vaccine.

None of the four challenged foals (Group 3) containing ERP colostrum antibody became sick or depressed like the challenged foals lacking ERP colostrum antibody.

It was apparent that the foals normal body temperature was higher than their adult counterparts. Also, environmental stress, such as handling the foals and laying in the hot sun appeared to have a greater influence on temperature fluctuations. A tendency toward a leukopenia appears to occur generally in the vaccinated foals between 3 to 7 days. The leukopenia is more severe in the challenged control foals than in the vaccinated foals.

A marked febrile response between 2 to 6 days after infection was noted in the challenged foals lacking ERP passive antibody. There appears to be no consistent temperature rise following ERP vaccination or ERP challenged foals with high levels of ERP passive antibody. One colt (155) exhibiting the lowest neutralizing ERP antibody (1:64) showed a temperature rise similar to control challenge colts, however, no depression or anorexia was noticed.

The following salient points may be extracted from experimental data obtained.

1. The Vero cellk cold-adapted (26°) virus replicates in vivo when given I.M., producing a protective (humoral and cell mediated) immunity against virulent ERP challenge virus administered intranasally.
2. The vaccine virus is non-pathogenic when given to pregnant mares and to foals coming from various ERP immunological backgrounds.
3. The vaccine virus can be isolated from horses having had previous ERP exposure (as measured by ERP neutralizing antibody) or from animals with no neutralizing antibody. The virus may be frequently recovered from washed blood leukocytes or infrequently from nasal turbinates.
4. The ERP vaccine virus is not transmitted to contact control horses, based on servo non-conversion of contact control animals, and upon negative virus isolation data from control animals.
5. Neutralizing serologies from vaccinated animals compare favorably with those induced by virulent ERP challenge virus.
6. Higher titer colostral ERP antibody passively transferred to foals apparently protects (no visible symptoms) the foals against virulent challenge ERP virus.
7. Cell mediated immunity appears to play an important part in protecting horses against ERP abortions and clinical signs of ERP, however, no feasible way has yet been found to measure ERP cellular immunity other than direct challenge experiments.

The number of virus isolates recovered following vaccinations with a replicating ERP vaccine or ERP virulent virus exposure is dependent largely upon the type and degree of immunity that the host exhibits. Virus isolations from foals with high levels of colostral ERP neutralizing antibody are quite prevalent. These foals are considered to have humoral immunity, and which depending upon the degree, does ameliorate symptomatology when challenged with virulent virus. However, humoral immunity plays little, if any, part in shutting off a virus carrier state. In contrast, active immunity induced with virus infection, be it a replicating vaccine virus or virulent virus, induces both cell mediated and humoral immunity. It is apparent from the data that after re-exposure to replicating vaccine virus or virulent virus, the virus carrier state is practically eliminated; however, it is not absolute. This appears to exist in non-ERP sensitized animals, and in previously ERP sensitized animals, based on serologies. It is obvious that cellular immunity, like humoral immunity, wanes with time. The time interval involved with depletion of ERP cellular immunity is unknown at this time.

8. The ERP vaccine virus does not cross the placental barrier, based on negative neutralizing pre-colostral serum samples from eight newborn foals. Also, no positive equine Herpes I vaccine virus was isolated from 18 newborn foals, from vaccinated-challenged mares. It also appears that passively acquired ERP neutralizing antibody depletion curves on five foals in isolation are uninterrupted in their decline, indicating no in utero exposure of Herpes I virus as there appears to be no active induction of Herpes I antibody.

9. ERP vacine virus isolations were more frequently recovered from blood leukocytes than from the nasal turbinates. This finding also applied to intranasally administered vaccine virus. Although only two principals out of four produced isolates, all were from blood leukocytes. Many of the nasal virus (vaccine) isolations recovered in the experiments may have originated from minute amounts of blood absorbed from capillaries damaged in the process of taking samples with six inch long nasal swabs from animals in motion. Of course, some nasal swab samples were lost due to bacteria and mold contamination.

10. Three overt cases of clinical stranglers occurred, and many isolations of *Streptococcus zooepidemicuc, Strep. equisimilis*, strep-Group E. *Staph Aureus* and one foal was found to have *Streptococcus equi*. These bacteria were periodically isolated from on-test animals. All of these bacteria have the capability of producing clinical signs of fever and/or nasal drainage, therefore, they were frequently monitored to help determine the cause of any clinical abnormality which might tend to confuse the results obtained from on-test animals. In most instances, the bacterial flare-ups were quite obvious when the horse temperature and total leukocyte charts are reviewed.

*Streptococcus zooepidemicus* is frequently a companion agent with the Equine Rhinopneumoniitis virus which is not surprising in view of its ubiquitous nature in the equine population. It would seen that any severe stress of the horse might incite *Strep. zooepidemicus* to flare up.

To summarize briefly, this invention relates to a vaccine and to its method of preparation. A virulent A183 isolate of an Equine I virus is introduced into a monolayer of a Vero permanent cell line which is incubated 3 to 5 days at 37° C. and cytopathology of the cells was completed. A freshly prepared stable cell monolayer of Vero cells was inoculated with a portion of the produced harvested virus. The culture was again incubated to produce cytopathology of at least a portion of the tissue cells. Thereafter, a portion of the virus produced was serially passed at least 30 times at an incubation temperature of 26° C. and the immunologically active live avirulent virus was recovered.

As will be readily apparent to those skilled in the art upon reading the above detailed description and examples, various modifications can be made thereto without departing from the spirit of the present invention and such scope of said invention shall be limited only by the scope of the appended claims.

What is claimed is:

1. A process for the production of an immunogenically active attenuated live equine rhinopneumonitis virus which comprises the steps of:
    (a) introducing a live virulent equine rhinopneumonitis virus into a Vero cell culture;
    (b) incubating the culture until the cellular cytopathology becomes evident;
    (c) harvesting a portion of the virus so produced and reintroducing the harvested virus into fresh tissue cultures;
    (d) repeating serial passage of the virus in tissue culture a sufficient number of times at a temperature within the range of from about 23° to about 33° C; to produce an immunogenically active live avirulent virus; and
    (e) recovering said virus from said tissue culture medium.

2. A process according to claim 1 wherein the incubation temperature of each serial passage is about 26° C.

3. A process according to claim 1 wherein the serial passage is carried out a least thirty times.

4. A process according to claim 1 wherein at least 50 serial passages are carried out at incubation of from 23° to about 33° C.

5. A process for the production of immunogenically active attenuated live equine rhinopneumonitis virus which comprises the steps of:
    (a) introducing a live virulent equine rhinopneumonitis virus into a monolayer of a Vero permanent cell line;
    (b) incubating the culture from about 3 to about 5 days at a temperature of 37° C. until cytopathology of the cells is substantially complete;
    (c) harvesting a portion of the virus so produced and introducing the harvested virus into a freshly prepared stable cell monolayer of Vero cells.
    (d) incubating said culture at a temperature of about 26° C. for a period of time sufficient to result in cytopathology of at least a portion of the tissue cells;
    (e) serially passing a portion of the virus so produced in stable vero cells at least 45 times at an incubation temperature of about 26° C. to produce an immunogenically active live avirulent virus; and
    (f) recovering said virus from said last serial passage.

6. An attenuated live equine rhinopneumonitis virus vaccine containing an effective quantity of immunogenically active avirulent live equine herpes I virus produced by a process which comprises the steps of:
    (a) introducing a live virulent equine herpes I virus into a Vero cell culture;
    (b) incubating the culture until the cellular cytopathology becomes evident;

(c) harvesting a portion of the virus so produced and re-introducing the harvested virus into fresh tissue culture;

(d) repeating serial passage of the virus in tissue culture a sufficient number of times at a temperature within the range of from about 23° to about 33° C. to produce an immunogenically active live avirulent virus.

(e) recovering said virus from said tissue culture medium; and (f) adding said recovered virus to a stabilizing solution to form a vaccine therefrom.

7. A vaccine according to claim 6 wherein the incubation temperature of each serial passage is about 26° C.

8. A vaccine according to claim 6 wherein the serial passage is carried out at least thirty times.

9. A vaccine according to claim 6 passages are carried out at incubation temperature of from about 23° to about 33° C.

10. An attenuated live equine rhinopneumonitis virus vaccine containing an effective quantity of immunogenically active avirulent live equine rhinopneumonitis virus produced by a process which comprises the steps of:

(a) introducing a live virulent equine rhinopneumonitis virus into a monolayer of a Vero permanent cell line;

(b) incubating the culture from about 3 to about 5 days at a temperature of 37° C until cytopathology of the cells is substantially complete;

(c) harvesting a portion of the virus so produced and introducing the harvested virus into a freshly prepared stable cell monolayer of Vero cells (d) incubating said culture at a temperature of about 26° C. for a period of time sufficient to result in cytopathology of at least a portion of the tissue cells;

(e) serially passing a portion of the virus so produced in stable Vero cells at least 45 times at an incubation temperature of about 26° C. to produce an immunogenically active live avirulent virus; and (f) recovering said virus from said last serial passage.

11. The method of protecting members of the family Equidae from equine rhinopneunominitis virus infection which comprises administering to said horses an effective dose of a live attenuated ERP virus vaccine prepared by a process which comprises the steps of:

(a) introducing a live virulent ERP virus into a Vero cell culture;

(b) incubating the culture until the cellular cytopathology becomes evident;

(c) harvesting a portion of the virus so produced and reintroducing the harvested virus into fresh tissue culture;

(d) repeating serial passage of the virus in tissue culture a sufficient number of times at a temperature within the range of about 23° to about 33° C. to produce an immunogenically active avirulent virus; and (e) recovering said virus from said tissue culture medium.

12. A method according to claim 11 wherein the incubation temperature of each serial passage is about 26° C.

13. A method according to claim 11 wherein the serial passage is carried out at least thirty times.

14. A method according to claim 11 wherein at least 50 serial passages are carried out at incubation temperatures of from about 23° to about 33° C.

15. The method of protecting equines from ERP virus infection which comprises administering to said equines an effective dose of a live attenuated ERP virus vaccine prepared by a process which comprises the steps of:

(a) introducing a live virulent ERP virulent ERP virus into a monolayer of a tissue cell culture derived from Vero cells;

(b) incubating the culture from about 3 to about 5 days at a temperature of 35° C. until cytopathology of the cells is substantially completed;

(c) harvesting a portion of the virus so produced and introducing the harvested virus into a freshly prepared monolayer of Vero cells.

(d) incubating said culture at a temperature of about 26° C. for a period of time sufficient to result in cytopathology of at least a portion of the cells;

(e) serially passing a portion of the virus so produced in Vero cells at least fifty times at an incubation temperature of about 26° C. to produce an immunogenically active live avirulent virus; and (f) recovering said virus from said last serial passage.

* * * * *